United States Patent [19]

Starchevich

[11] Patent Number: 5,328,487

[45] Date of Patent: Jul. 12, 1994

[54] INTRAVENOUS TUBE MOUNTING AND CONTROL APPARATUS

[76] Inventor: Jovanka Starchevich, 138 Sullivan St., New York, N.Y. 10012

[21] Appl. No.: 949,148

[22] Filed: Sep. 23, 1992

[51] Int. Cl.⁵ .............................................. A61M 5/00
[52] U.S. Cl. ................................. 604/246; 604/180; 128/DIG. 6
[58] Field of Search ................... 604/118, 65, 67, 131, 604/253, 260, 246, 247, 34, 80, 250, 257, 180; 128/DIG. 6, DIG. 12, DIG. 13; 251/6, 9; 248/74.1, 74.2, 75

[56] References Cited

U.S. PATENT DOCUMENTS

| | | |
|---|---|---|
| 3,915,167 | 10/1975 | Waterman . |
| 4,170,995 | 10/1979 | Levin et al. ........................ 604/180 |
| 4,606,735 | 8/1986 | Wilder et al. ...................... 604/189 |
| 5,005,793 | 4/1991 | Shillington . |
| 5,014,962 | 5/1991 | Adelberg . |
| 5,238,218 | 8/1993 | Mackal ............................... 251/10 |
| 5,259,587 | 11/1993 | D'Alessio et al. .................. 251/4 |

FOREIGN PATENT DOCUMENTS 0448202 3/1968 Switzerland .................. 248/74.1

*Primary Examiner*—C. Fred Rosenbaum
*Assistant Examiner*—V. Alexander
*Attorney, Agent, or Firm*—R. Neil Sudol; Henry D. Coleman

[57] ABSTRACT

Apparatus for engaging at least one associated intravenous tube used in the delivery of medication or nutrient to a patient which includes a first generally U-shaped member having first and second generally straight elongated legs. Each of the legs has inner and outer faces. The inner faces are disposed in opposed relation and the first leg is movable between a first position in which the respective inner faces of the first and second legs are disposed in spaced relation and a second position in which the respective inner faces of the first and second legs are closer than in the first position, the inner faces being disposed in the first position with a space sufficient to allow insertion of an intravenous tube therebetween, the inner faces being dimensioned and configured to engage the sides of the associated intravenous tube in the second position.

21 Claims, 3 Drawing Sheets

INTRAVENOUS TUBE MOUNTING AND CONTROL APPARATUS

BACKGROUND OF THE INVENTION

The invention relates to apparatus for mounting intravenous tubes and for controlling the flow of fluids through intravenous tubes. Intravenous tubes have been widely used for supply nutrients and medication to patients. In many cases the same patient may have more than one such tube connected to his or her body. In some case several tubes may be connected to each of several patients that are located in adjacent beds. In emergency situations it is of great importance to be able to quickly determine with absolute certainty which tube is connected to which patient and which nutrient or medication.

At least some of the prior art devices are extremely difficult to use. More specifically, at least one uses the combination of an inclined plane and a roller that is moved along the inclined plane to allow more or less flow through the intravenous tube. The so-called Adelberg clamp is delivered pre-assembled to the tube by the manufacturer or are delivered by the manufacturer as a set. Other devices are designed such that it is essential to have access to a free end of the intravenous tube because the clamp can only be slipped on the free end.

It is an object of the invention to provide a construction that will enable the easy identification of each intravenous (IV) tube quickly.

It is another object of the invention to provide apparatus that will enable the health care professional to alternatively to completely shut off flow or to modulate the flow to allow selection of a desired flow rate.

It is still another object of the invention to provide apparatus which is inexpensive to manufacture.

It is also an object of the invention to provide apparatus that will work with any of various standard size intravenous tubing sizes.

Yet another object of the invention is to provide apparatus that facilitates organization a large number of tubes to prevents accidental shutoff or other changes in the wrong tube.

SUMMARY OF THE INVENTION

It has now been found that these and other objects of the invention may be attained in an apparatus for engaging at least one associated intravenous tube used in the delivery of medication or nutrient to a patient which includes a first generally U-shaped member having first and second generally straight elongated legs, each of the legs having inner and outer faces, the inner faces being disposed in opposed relation, the first leg being movable between a first position in which the respective inner faces of the first and second legs are disposed in spaced relation and a second position in which the respective inner faces of the first and second legs are closer than in the first position, the inner faces being disposed in the first position with a space sufficient to allow insertion therebetween, the inner faces being dimensioned and configured to engage the sides of the associated intravenous tube in the second position.

In some forms of the invention the apparatus further includes a second generally U-shaped member having first and second sides, the first and second sides, the first and second sides engaging the outer faces of the first and second legs of the first generally U-shaped member. The second generally U-shaped member may be slidable along a portion of the axial extent of the first and second legs. In some cases the apparatus includes means for engaging one of the legs of one of the first U-shaped member to one of the sides of the second U-shaped member.

The means for engaging may include an elongated slot in an outer face of one of the legs of the first U-shaped member. The means for engaging may include an axial extremity of one of the sides of the second U-shaped member having means for meshing with the elongated slot to permit sliding engagement. The first and second legs of the first generally U-shaped member may each have jaws on the inner faces thereof that are disposed in opposed relationship and that are dimensioned and configured to squeeze the associated intravenous tube in the second position. The apparatus may further include a generally planar base that carries the first generally U-shaped member. The base includes a V-shaped slot, in some forms of the invention, dimensioned and configured to permit insertion therein of the associated intravenous tube in a manner to shut off fluid flow in the intravenous tube.

The apparatus may further include means for partially blocking intravenous tube access to the V-shaped slot, the means for blocking being disposed proximate to the open end of the V-shaped slot. The geometric axis of the V-shaped slot and the first generally U-shaped slot may be aligned and the apparatus may further includes a surface for placement of identifying indicia proximate to the first U-shaped member. In some forms of the invention the apparatus further includes a generally L-shaped member extending from the base. The L-shaped member may be dimensioned and configured to retain the associated intravenous tube in the first U-shaped member and may be disposed intermediate the first U-shaped member and the V-shaped slot. The apparatus may further includes means for securing the associated intravenous tubing to the base disposed further from the V-shaped slot than from the first U-shaped member.

In many forms of the invention the apparatus includes at least two identical apparatus for engaging respective intravenous tubes.

BRIEF DESCRIPTION OF THE DRAWING

The invention will be better understood by reference to the accompanying drawing in which.

DESCRIPTION OF THE PREFERRED EMBODIMENT

Figure 1:
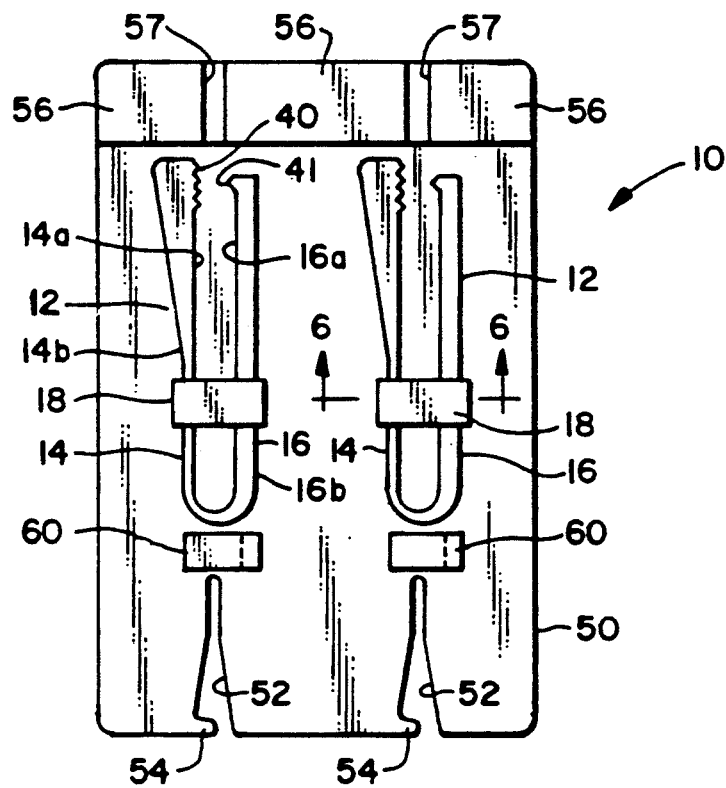
FIG. 1 is a plan view of an apparatus in accordance with one form of the invention.

Referring now to FIGS. 1-8 there is shown a an apparatus 10 for engaging at least one associated intravenous tube A used in the delivery of medication or nutrient(s) to a patient which includes a first generally U-shaped members 12 having first and second generally straight elongated legs 14, 16. Each of the legs 14, 16 have inner faces 14a and outer faces 14b. The inner faces 14a, 16a are disposed in opposed relation. The first leg 14 is movable between a first position in which the respective inner faces 14a, 16a of the first and second legs 14, 16 are disposed in spaced relation and a second position in which the respective inner faces 14a, 16a of the first and second legs 14, 16 are closer than in the first position. The inner faces 14a, 16a are disposed in the first position, illustrated in FIG. 1, with a space therebetween that is sufficient to allow insertion of an associated intravenous tube A. In the second position, illustrated in FIG. 7, the tube A is squeezed to shut off or modulate the flow through the intravenous tubing.

The apparatus further includes a second generally U-shaped member 18 having first and second sides 18a, 18b. The first and second sides 18a, 18b engage the outer faces 14b, 16b of the first and second legs 14, 16 of the first generally U-shaped member 12. The second generally U-shaped member 18 may be slidable along a portion of the axial extent of the first and second legs 12, 14. As will be apparent from FIG. 6B the member 18 may be pivoted sufficiently to permit installation of the tube A by merely slipping an axial section under the member 18 and within the legs of the member 12. In other words it is not necessary to "thread" the end of the tube into the apparatus 10 as is the case with some prior art apparatus.

Figure 6B:
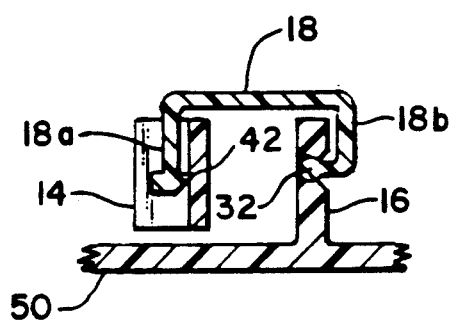
FIG. 6B is a view similar to the view of FIG. 6A showing an alternate position of the slider.
Figure 6A:
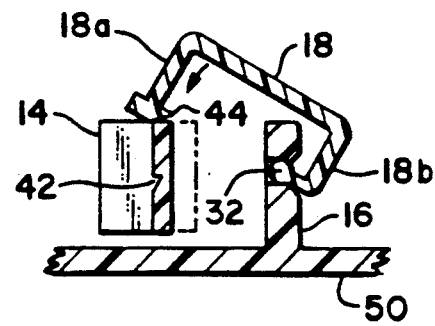
FIG. 6A is a fragmentary sectional view taken along the line 6—6 of FIG. 1.
Figure 7:
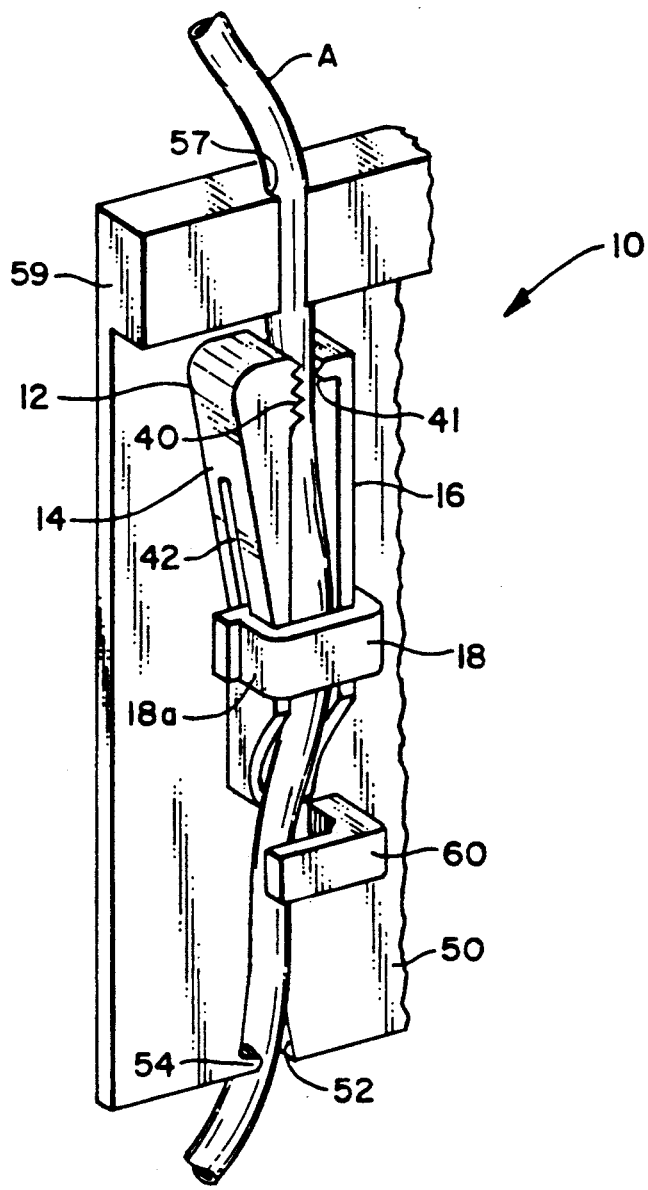
FIG. 7 is a fragmentary perspective view of a portion of the apparatus of FIG. 1.
Figure 8:
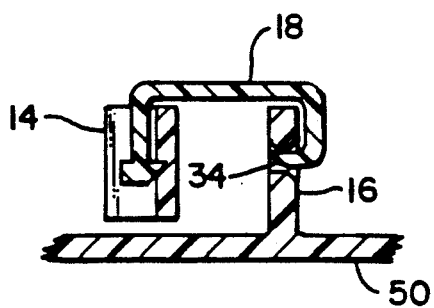
FIG. 8 is a view similar to FIG. 6A similar to that of FIG. 6A illustrating an alternative structure.

Preferably, the apparatus 10 includes means for engaging one of the legs of one of the first U-shaped member to one of the sides of the second U-shaped member 8. The means for engaging, in the preferred embodiment, includes an elongated slot 30 in the outer face 16b of the leg 16 of the first U-shaped member 12. In the preferred embodiment the means for engaging include an either a cylindrical section shaped axial extremity 32 (as shown in FIGS. 6A and 6B) or a hook shaped axial extremity 34 (as shown in FIG. 8) which slide in and engage respectively with either a cylindrical section shaped slot 30 or a rail shaped edge of the slot 30.

The first and second legs 14, 16 of the first generally U-shaped member 12 each have jaws on the inner faces 14a, 16a thereof that are disposed in opposed relationship and that are dimensioned and configured to squeeze the associated intravenous tube in the second position. More specifically, the first leg may be provided with a plurality of laterally extending teeth 40 on the inner face 14a thereof. The inner face 16 has a single laterally extending ridge shaped surface 41 intended to concentrate forces against the intravenous tube A to either modulate or shut off fluid flow in the tube A. A groove 42 in the outer wall 14b is elongated and engages a detent 44 on the outer face 14b of the leg 14.

In the preferred embodiment the apparatus 10 includes a generally planar base 50 that carries the first generally U-shaped member as best seen in FIGS. 1-3, 6A, and 6B. The base 50 includes a V-shaped slot 52 dimensioned and configured to permit insertion therein of the associated intravenous tube A in a manner to shut off fluid flow in the intravenous tube A.

The apparatus 10 may further include means for partially blocking intravenous tube A access to the V-shaped slot 52. The means for blocking is disposed proximate to the open end of the V-shaped slot and is preferably a laterally extending member 54 that partially blocks access to the V-shaped slot 52. This ensures that the tube A does not accidentally fall into the V-shaped slot and thus inadvertently get shutoff.

The geometric axis of the V-shaped slot 52 and the first generally U-shaped member are aligned and the apparatus may further include surfaces 56 for placement of identifying indicia proximate to the first U-shaped member 12. The apparatus preferably includes a generally L-shaped member 60 extending from the base. The L-shaped member 60 is preferably dimensioned and configured to retain the associated intravenous tube A in the first U-shaped member and is disposed intermediate the first U-shaped member 12 and the V-shaped slot 52. A slot 57 is preferable disposed in a step shaped part 59 of the base 50 in aligned relation to the geometric axes of the v-shaped slot and the first U-shaped member 12. In various forms of the invention the slot 57 may be cylindrical section shaped (not shown) or alternatively have opposed flat mutually parallel walls (not shown). The positive retention of the tube A in the slot 57 is important even if the member 12 is not engaging the tube A. More specifically, the positive location of the tubes A is essential to proper identification of respective tubes and thus avoidance of errors as the result of confusing the tubes.

It will be seen that slot 57 is a means for securing the associated intravenous tubing A to the base 50 and that the slot 57 is disposed further from the V-shaped slot 52 than from the first U-shaped member 12.

Figure 2:
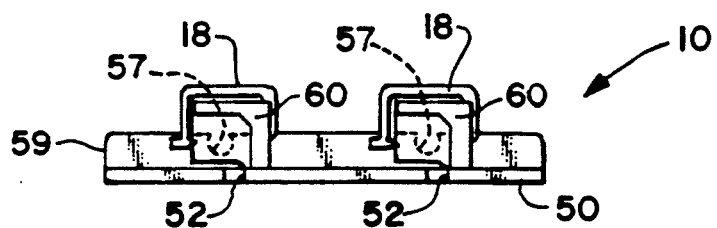
FIG. 2 is front elevational view of the apparatus shown in FIG. 1.
Figure 3:
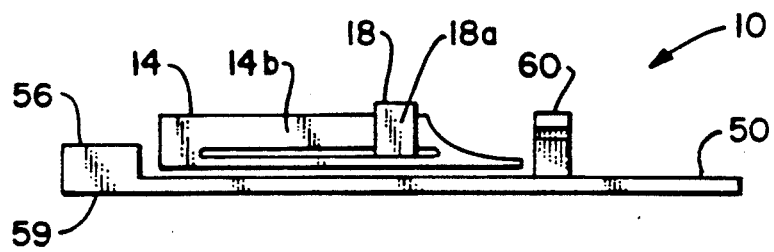
FIG. 3 is left elevational view of the apparatus shown in FIG. 1.
Figure 4:
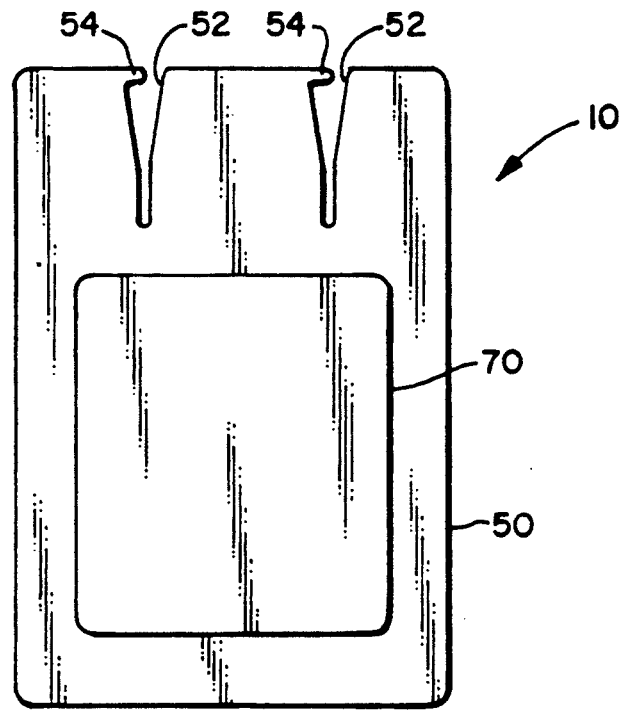
FIG. 4 is a bottom view of the apparatus shown in FIG. 1.
Figure 5:
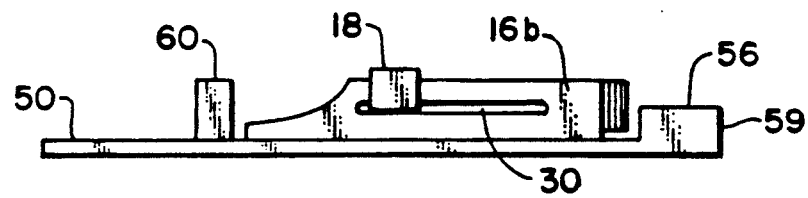
FIG. 5 is right elevational view of the apparatus shown in FIG. 1.

Although for simplicity the FIGS. 1-2 of the present application show only two discreet clamping apparatus it will be apparent that other embodiments of the invention may have a much larger number. Such arrangement facilitate the orderly placement of the intravenous tubes with a minimum of risk or error.

In some forms of the invention the base 50 is provided mounting surface 70 which in the preferred embodiment cooperates with the a band (not shown) that typically will extend around the pole (not shown) which supports the intravenous fluid bottles (not shown), Various other mounting means will be apparent to those skilled in the art.

It will be seen that the apparatus in accordance allows the user to modulate the flow through the tube A by sliding the second U-shaped member along the legs 14, 16 to cause the desired flow modulation or shutoff. The V-shaped slot is intended as a secondary shutoff means to absolutely insure no inadvertent fluid flow in the tube A.

A major advantage of the apparatus in accordance with the invention is that the user may easily slip the tube A into the first U-shaped member 12. The ease of insertion will be apparent to those skilled in the field.

The invention has been described with reference to its illustrated preferred embodiment. Persons skilled in the art of such devices may upon exposure to the teachings herein, conceive other variations. Such variations are deemed to be encompassed by the disclosure, the invention being delimited only by the following claims.

Having thus described my invention I claim:

1. An apparatus for engaging at least one associated intravenous tube used in the delivery of medication or nutrient to a patient, which comprises:

a first generally U-shaped member having first and second generally straight elongated legs, each of said legs having inner and outer faces, said inner faces being disposed in opposed relation, said first leg being movable between a first position in which the respective inner faces of said first and second legs are disposed in spaced relation and a second position in which the respective inner faces of said first and second legs are closer than in said first position, said inner faces being disposed in said first position with a space sufficient to allow insertion of the associated intravenous tube between said legs, said inner faces being dimensioned and configured to engage the sides of the associated intravenous tube in said second position, a second generally U-shaped member engaging said legs along said outer faces thereof, said second generally U-shaped member being slidable in an axial direction along said legs, whereby said first leg is shiftable between said first position and said second position.

2. The apparatus as described in claim 1 wherein:
said apparatus includes means for engaging one of said legs of one of said first U-shaped member to one of said sides of said second U-shaped member.

3. The apparatus as described in claim 2 wherein:
said means for engaging includes an elongated slot in an outer face of one of said legs of said first U-shaped member.

4. The apparatus as described in claim 3 wherein:
said means for engaging includes an axial extremity of one of said sides of said second U-shaped member having means for meshing with said elongated slot that permit sliding engagement.

5. The apparatus as described in claim 4 wherein:
said first and second legs of said first generally U-shaped member each having jaws on the inner faces thereof, said jaws being disposed in opposed relationship and being dimensioned and configured to squeeze the associated intravenous tube in said second position.

6. The apparatus as described in claim 5 wherein:
said apparatus further includes a generally planar base, said base carrying said first generally U-shaped member.

7. The apparatus as described in claim 6 wherein:
said base include a V-shaped slot dimensioned and configured to permit insertion therein of the associated intravenous tube in a manner to shut off fluid flow in the intravenous tube.

8. The apparatus as described in claim 7 wherein:
said apparatus further includes means for partially blocking intravenous tube access to said V-shaped slot, said means for blocking being disposed proximate to the open end of said V-shaped slot.

9. The apparatus as described in claim 8 wherein:
the geometric axis of said V-shaped slot and said first generally U-shaped member are aligned.

10. The apparatus as described in claim 9 wherein:
said apparatus further includes a surface for placement of identifying indicia proximate to said first U-shaped member.

11. The apparatus as described in claim 10 wherein:
said apparatus further includes a generally L-shaped member extending from said base, said L-shaped member being dimensioned and configured to retain the associated intravenous tube in said first U-shaped member.

12. The apparatus as described in claim 11 wherein:
said L-shaped member is disposed intermediate said first U-shaped member and said V-shaped slot.

13. The apparatus as described in claim 12 wherein:
said apparatus further includes means for securing the associated intravenous tubing to said base disposed further from said V-shaped slot than from said first U-shaped member.

14. A flow regulator for intravenous tubing, comprising:
a clamping member having elongate first and second clamping elements, said clamping elements having inner faces facing one another; and
means for shifting said clamping elements alternately towards and away from one another to vary a fluid flow cross-section in an intravenous tube inserted between said clamping elements, said means for shifting including a slider member attached to said clamping elements and slidable in a generally axial direction therealong.

15. The flow regulator defined in claim 14 wherein said means for shifting further includes a camming surface on an outer face of at least one of said clamping elements, whereby a longitudinal motion of said slider member along said clamping elements produces a transverse motion of said one of said clamping elements towards the other of said clamping elements.

16. The flow regulator defined in claim 14, further comprising means on at least one of said inner faces for engaging and pinching an intravenous tube inserted between said clamping elements.

17. The flow regulator defined in claim 16 wherein said means for engaging and pinching includes an inwardly extending tooth on said one of said inner faces.

18. The flow regulator defined in claim 14 wherein said slider member is generally U-shaped and is pivotably attached to one of said clamping elements for enabling a temporary separation of said slider member from the other of said clamping elements to enable alternate insertion and removal of the intravenous tubing from between said clamping elements.

19. The flow regulator defined in claim 18 wherein the other of said clamping elements is provided with an elongated slot in the outer face of said other of said clamping elements, said slider member being provided with means for meshing with said elongated slot to permit sliding of said slider member relative to said one of said clamping elements.

20. The flow regulator defined in claim 14 wherein said clamping member is generally U-shaped and said clamping elements are legs of said clamping member.

21. A method for use in intravenous feeding, comprising the steps of:
providing a flow regulator comprising a clamping member having elongate first and second clamping elements, said clamping elements having inner faces facing one another and further comprising means for shifting said clamping elements alternately towards and away from one another, said means for shifting including a slider member attached to said clamping elements;
inserting an intravenous tube between said clamping elements;
sliding said slider member in a generally axial direction along said clamping elements; and
during motion of said slider member along said clamping elements, moving said clamping elements relatively towards one another by virture of said step of sliding, thereby pinching said intravenous tube between said clamping elements to vary a fluid flow cross-section in said intravenous tube.

* * * * *

UNITED STATES PATENT AND TRADEMARK OFFICE
CERTIFICATE OF CORRECTION

PATENT NO. : 5,328,487
DATED : July 12, 1994
INVENTOR(S) : Jovanka Starchevich

Page 1 of 2

It is certified that error appears in the above-indentified patent and that said Letters Patent is hereby corrected as shown below:

Column 1, line 9, change "supply" to --supplying--; line 12, change "case " to --cases--; line 24, change "are" to --is--; line 32, delete "to"; line 41, insert --of-- after "organization"; line 42, change "prevents" to --prevent--; line 60, insert --of an IV tube-- after "insertion"; line 65, delete "first and second sides, the" (first occurrence).

Column 2, line 30, change "cludes" to --clude--; line 39, change "includes" to --include--; line 44, change "apparatus" to --apparatuses--; line 49, change "drawing" to --drawings--; line 67, delete "similar to FIG. 6A".

Column 3, line 4, delete "a"; line 8, change "members" to --member--; line 10, insert --,16a-- after "14a"; line 10, insert --16b-- after "14b"; line 29, delete "12,"; line 30, insert --,16-- after "14"; line 30, change "6B" to --6A--; line 36, change "apparatus" to --apparatuses--; line 38, delete "one of" (second occurrence); line 39, insert --12-- after "ber"; line 40, change "8" to --18--; line 44, delete "an"

Column 4, line 19, change "preferable" to --preferably--; line 21, change "v-shaped" to --V-shaped--; line 36, change "apparatus" to --apparatuses--; line 39, change "ment" to --ments--; line 43, delete "the"; line 48, insert --with this invention-- after "accordance".

UNITED STATES PATENT AND TRADEMARK OFFICE
CERTIFICATE OF CORRECTION

PATENT NO. : 5,328,487
DATED : July 12, 1994
INVENTOR(S) : Jovanka Starchevich

It is certified that error appears in the above-indentified patent and that said Letters Patent is hereby corrected as shown below:

Column 5, line 23, claim 2, delete "one of".

Column 5, line 46, claim 7, change "include" to --includes--.

Column 6, line 64, claim 21, change "virture" to --virtue--.

Signed and Sealed this

Thirtieth Day of May, 1995

*Attest:*

BRUCE LEHMAN

*Attesting Officer*    *Commissioner of Patents and Trademarks*